United States Patent
Cosmescu (10) Patent No.: US 11,350,980 B2
(45) Date of Patent: Jun. 7, 2022

(54) ULTRAPOLAR NON-TELESCOPIC ELECTROSURGERY PENCIL WITH ARGON BEAM CAPABILITY AND ULTRAPOLAR ELECTROSURGERY BLADE ASSEMBLY

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 0 days.

(21) Appl. No.: 16/896,875

(22) Filed: Jun. 9, 2020

(65) Prior Publication Data
US 2020/0297404 A1    Sep. 24, 2020

Related U.S. Application Data

(63) Continuation of application No. 15/909,326, filed on Mar. 1, 2018, now Pat. No. 11,147,605.

(Continued)

(51) Int. Cl.
*A61B 18/00* (2006.01)
*A61B 18/04* (2006.01)
(Continued)

(52) U.S. Cl.
CPC ........ *A61B 18/042* (2013.01); *A61B 18/1402* (2013.01); *A61B 2017/00991* (2013.01);
(Continued)

(58) Field of Classification Search
CPC .............. A61B 18/042; A61B 18/1402; A61B 2018/00077; A61B 2218/005;
(Continued)

(56) References Cited

U.S. PATENT DOCUMENTS

| | | | |
|---|---|---|---|
| 4,161,950 A | 7/1979 | Doss et al. | |
| 4,248,231 A | 2/1981 | Herczog et al. | |
| 5,244,462 A * | 9/1993 | Delahuerga | A61B 18/042 606/37 |
| 6,099,525 A * | 8/2000 | Cosmescu | A61B 18/00 606/41 |

(Continued)

*Primary Examiner* — Jaymi E Della
*Assistant Examiner* — Rachel A. Vierra
(74) *Attorney, Agent, or Firm* — Zeman-Mullen & Ford, LLP (57) ABSTRACT

Ultrapolar non-telescopic electrosurgery pencil with argon beam capability which is capable of using monopolar energy in a bipolar mode for cutting and coagulation and which is also capable of using an ionized gas for cutting and coagulation. The ultrapolar non-telescopic electrosurgery pencil with argon beam capability includes a handpiece member, an electrosurgery blade assembly positioned within an end of the handpiece member where the electrosurgery blade assembly includes a blade having a non-conductive sharp cutting edge, a return electrode, and an active electrode, and a non-conductive hollow tube member positioned over a top of the blade and at least a portion of the return electrode, a first conductive hollow tube having at least a portion concentrically contained within the non-conductive hollow tube member of the electrosurgery blade assembly, a flexible non-conductive tube contained within at least a portion of ultrapolar non-telescopic electrosurgery pencil which provides a gas to the first conductive hollow tube, and a plurality of electrical conductors for connecting the return electrode, the active electrode, and the first conductive hollow tube to an RF electrosurgical generator for activating the ultrapolar non-telescopic electrosurgery pencil.

18 Claims, 4 Drawing Sheets

Related U.S. Application Data (60) Provisional application No. 62/465,708, filed on Mar. 1, 2017, provisional application No. 62/465,729, filed on Mar. 1, 2017.

(51) Int. Cl.
- *A61B 18/14* (2006.01)
- *A61B 17/00* (2006.01)
- *A61B 18/12* (2006.01)

(52) U.S. Cl.
CPC ............ *A61B 2018/00077* (2013.01); *A61B 2018/00083* (2013.01); *A61B 2018/0091* (2013.01); *A61B 2018/00607* (2013.01); *A61B 2018/1246* (2013.01); *A61B 2018/1412* (2013.01); *A61B 2218/005* (2013.01)

(58) Field of Classification Search
CPC .......... A61B 2018/00607; A61B 2018/0091; A61B 2018/1246; A61B 2018/1412; A61B 2018/00083
See application file for complete search history.

(56) References Cited

U.S. PATENT DOCUMENTS

| | | | |
|---|---|---|---|
| 7,112,199 B2 | 9/2006 | Cosmescu | |
| 7,947,037 B1* | 5/2011 | Garito | A61B 18/14 |
| | | | 606/41 |
| 10,507,053 B2* | 12/2019 | Cosmescu | A61B 18/042 |
| 10,512,500 B2* | 12/2019 | Cosmescu | A61B 18/042 |
| 10,792,095 B2* | 10/2020 | Cosmescu | A61B 18/1402 |
| 2004/0024396 A1 | 2/2004 | Eggers | |
| 2004/0181213 A1* | 9/2004 | Gondo | A61B 18/1402 |
| | | | 606/45 |
| 2005/0113825 A1* | 5/2005 | Cosmescu | A61B 18/1402 |
| | | | 606/45 |
| 2010/0094283 A1 | 4/2010 | Cosmescu | |
| 2012/0116397 A1* | 5/2012 | Rencher | A61B 18/1402 |
| | | | 606/45 |
| 2016/0317209 A1 | 11/2016 | Cosmescu | |
| 2017/0360497 A1* | 12/2017 | Hancock | A61B 18/12 |
| 2018/0014875 A1 | 1/2018 | Cosmescu | |
| 2018/0092692 A1 | 4/2018 | Cosmescu | |
| 2018/0256243 A1* | 9/2018 | Cosmescu | A61B 18/042 |
| 2018/0256244 A1* | 9/2018 | Cosmescu | A61B 18/1402 |
| 2018/0263680 A1* | 9/2018 | Cosmescu | A61B 18/16 |
| 2020/0113618 A1* | 4/2020 | Cosmescu | A61B 18/042 |
| 2020/0121383 A1* | 4/2020 | Cosmescu | A61B 18/14 |

\* cited by examiner

ULTRAPOLAR NON-TELESCOPIC ELECTROSURGERY PENCIL WITH ARGON BEAM CAPABILITY AND ULTRAPOLAR ELECTROSURGERY BLADE ASSEMBLY

CROSS-REFERENCE TO RELATED APPLICATIONS

This application is a continuation of, and claims priority to, utility patent application having Ser. No. 15/909,326 filed Mar. 1, 2018 entitled "Ultrapolar Telescopic and Non-Telescopic Electrosurgery Pencils With Argon Beam Capability And Ultrapolar Electrosurgery. Blade Assembly" which is herein incorporated by reference in its entirety. This application also claims priority to provisional patent application having Ser. No. 62/465,729 entitled "Ultrapolar Electrosurgery Pencil With Argon Beam Capability," filed Mar. 1, 2017 and provisional patent application having Ser. No. 62/465,708 entitled "Ultrapolar Telescopic Electrosurgery Pencil With Argon Beam Capability," filed Mar. 1, 2017 which are both herein incorporated by reference in their entireties.

This application relates to provisional patent application having Ser. No. 62/383,855 entitled "Ultrapolar Electrosurgery Blade Assembly And Pencil For Use in ESU Monopolar and Bipolar Modes," filed Sep. 6, 2016, and its related utility patent application having Ser. No. 15/697,335 filed Sep. 6, 2017 and provisional patent application having Ser. No. 62/404,292 entitled "Ultrapolar Telescopic Electrosurgery Pencil," filed Oct. 5, 2016, and its related utility patent application having Ser. No. 15/725,640 filed Oct. 5, 2017 which are all herein incorporated by reference in their entireties.

FIELD OF INVENTION

The present invention is generally directed to ultrapolar telescopic and non-telescopic electrosurgery pencils with argon beam capability which are capable of using monopolar energy in a bipolar mode for cutting and coagulation and which is also capable of using an ionized gas for cutting and coagulation. The present invention is also directed to an ultrapolar electrosurgery blade assembly that is used in both the ultrapolar telescopic and non-telescopic electrosurgery pencils having argon beam capability.

BACKGROUND OF THE INVENTION

Electrosurgery uses an RF electrosurgical generator (also known as an electrosurgical unit or ESU) and a handpiece with an electrode to provide high frequency, alternating radio frequency (RF) current input at various voltages to cut or coagulate biological tissue. The handpiece may be a monopolar instrument with one electrode or a bipolar instrument with two electrodes. When using a monopolar instrument, a return electrode pad is attached to the patient and the high frequency electrical current flows from the generator, to the monopolar instrument, through the patient to the patient return electrode pad, and back to the generator. Monopolar electrosurgery is commonly used due to its versatility and effectiveness. However, the excessive heat generated with monopolar electrosurgery can cause excessive tissue damage and necrosis of the tissue because the return electrode positioned on the back of the patient causes high voltage and high RE energy to pass through the patient.

In bipolar electrosurgery, active output and patient return functions both occur at the surgery site because both the active and return electrodes are contained in the bipolar instrument. Therefore, the path of the electrical current is confined to the biological tissue located between the active and return electrodes. Although bipolar electrosurgery enables the use of lower voltages and less energy than monopolar electrosurgery and thereby reduces or eliminates the likelihood of tissue damage and sparking associated with monopolar electrosurgery, it has limited ability to cut and coagulate large bleeding areas.

It is also common to use argon beam coagulators during electrosurgery. In argon beam coagulation (ABC), current is applied to tissue by a directed beam of ionized argon gas which causes a uniform and shallow coagulation surface thereby stopping blood loss. However, argon beam enhanced cutting may also be performed using application of an ionized argon gas.

At present, electrosurgery is often the best method for cutting and argon beam coagulation is often the best method for cessation of bleeding during surgery. Surgeons typically need to switch between argon beam coagulation and electrosurgery modes depending on what is happening during the surgery and what they need to achieve at a particular point in the surgery such as cutting, or making incisions in tissue, or stopping the bleeding at the surgical site.

However, since surgical tools and devices currently available to surgeons require switching between these two methods during the surgical procedure, there is a need for a surgical device or tool that enables a surgeon or user to utilize the best methods used for cutting and cessation of bleeding at the surgical site at the same time, or simultaneously, in addition to being able to use them separately. An electrosurgery blade assembly with argon beam capability and telescopic and non-telescopic electrosurgery pencils with argon beam capability that utilize such an electrosurgery blade assembly can provide a user or surgeon with safe, efficient, effective, and flexible ways to both cut and coagulate tissue during electrosurgery. With this type of device, a user or surgeon can use monopolar energy in a bipolar mode for cutting and coagulation and can also use ionized gas for cutting and coagulation without excessive tissue damage and necrosis of the tissue.

The ultrapolar telescopic and non-telescopic electrosurgery pencils described with reference to the present invention can be used in both monopolar and bipolar modes thereby providing flexibility to a surgeon or operator. The ultrapolar telescopic electrosurgery pencil described with reference to the present invention also enables a user or surgeon to more easily and efficiently access the surgical site with enhanced viewing capability by extending the telescopic member of the pencil as well as the electrosurgery blade positioned within the telescopic member of the pencil. Embodiments of the ultrapolar telescopic and non-telescopic electrosurgery pencils described with reference to the present invention also enable a user or surgeon to evacuate smoke and/or debris from the surgical site while being able to perform precise cutting at the surgical site as well as cutting and coagulation of tissue areas located at the surgical site.

SUMMARY OF EXEMPLARY EMBODIMENTS

The exemplary embodiments of the ultrapolar telescopic and non-telescopic electrosurgery pencils with argon beam capability of the present invention enable a user or surgeon to perform cutting with the sharp non-conductive cutting edge of the electrosurgery blade, cutting with the active and return electrodes of the electrosurgery blade, coagulating large areas of biological tissue by using both active and return electrodes on the electrosurgery blade, and cutting and coagulating tissue using ionized gas that projects from the non-conductive hollow tube member that is positioned over a return electrode or an active electrode contained on the electrosurgery blade. A particularly new and innovative feature of the ultrapolar telescopic and non-telescopic electrosurgery pencils with argon beam capability of the present invention is the ability of a user or surgeon to simultaneously cut tissue with the sharp non-conductive cutting edge of the electrosurgery blade while coagulating tissue using ionized gas that projects from the non-conductive hollow tube member that is positioned over a return electrode or an active electrode contained on the electrosurgery blade. The ultrapolar telescopic and non-telescopic electrosurgery pencils with argon beam capability of the present invention provide a user or surgeon with safe, efficient, effective, and flexible ways to both cut and coagulate tissue during electrosurgery. The ultrapolar telescopic and non-telescopic electrosurgery pencils with argon beam capability of the present invention are much safer for the patient than other electrosurgery instruments and methods due to the fact that high voltage and high RF energy do not need to pass through the patient during electrosurgery. In addition, the telescoping ability of the ultrapolar telescopic electrosurgery pencil with argon beam capability of the present invention enables a user or surgeon to adjust the length of the ultrapolar electrosurgery pencil to better accommodate accessing different surgical sites.

Further, the ultrapolar telescopic and non-telescopic electrosurgery pencils with argon beam coagulation of the present invention can operate at extremely low power, such as 5 to 15 Watts. As a result, lateral damage to tissue is minimal during cutting with the ultrapolar telescopic and non-telescopic electrosurgery pencils of the present invention and the composition of the electrosurgery blade assembly used with the ultrapolar telescopic and non-telescopic electrosurgery pencils of the present invention minimizes the build-up of eschar and dead tissue on the surfaces of the blade during electrosurgical procedures thereby eliminating the need to stop a surgical procedure to clean off the electrosurgery blade.

The ultrapolar telescopic and non-telescopic electrosurgery pencils with argon beam capability are capable of using monopolar energy in a bipolar mode for cutting and coagulation using an electrosurgery blade. The ultrapolar telescopic and non-telescopic electrosurgery pencils with argon beam capability of the present invention are also capable of using an ionized gas for cutting and coagulation thereby providing a user or surgeon with a variety of ways to perform cutting and/or coagulation of tissue during an operative procedure.

In one exemplary embodiment, the ultrapolar electrosurgery blade assembly contained within the ultrapolar telescopic and non-telescopic electrosurgery pencils with argon beam capability of the present invention includes a non-conductive planar member having opposing planar sides and a sharp cutting edge, a return electrode located on one opposing planar side, an active electrode located on the opposite planar side, and a non-conductive hollow tube member positioned over a top of the non-conductive planar member and at least a portion of the return electrode. The return electrode may comprise a conductive return layer and a conductive return projection that is located within the non-conductive hollow tube member. This enables a gas supplied from a conductive hollow tube (such as that contained within a handpiece member of a non-telescopic electrosurgery pencil or within a hollow telescopic member of a telescopic electrosurgery pencil as later described with reference to the ultrapolar telescopic and non-telescopic electrosurgery pencils with argon beam capability of the present invention) into the non-conductive hollow tube member to be ionized as it comes into contact with a conductive active projection extending from the conductive hollow tube and the conductive return projection of the return electrode thereby enabling both cutting and coagulation of tissue without high voltage and high RF energy passing through the patient.

In one exemplary embodiment of the ultrapolar electrosurgery pencil with argon beam capability of the present invention, the ultrapolar electrosurgery pencil with argon beam capability is non-telescopic and includes a handpiece member having a first end, a second end, and a channel contained therein, an electrosurgery blade assembly positioned within the first end of the handpiece member where the electrosurgery blade assembly includes a non-conductive planar member with opposing planar sides and a sharp cutting edge, a return electrode located on one opposing planar side, an active electrode located on the other opposing planar side, and a non-conductive hollow tube member positioned over a top of the non-conductive planar member and at least a portion of the return electrode, a first conductive hollow tube having a first end and a second end where at least a portion of the first conductive hollow tube is concentrically contained within the non-conductive hollow tube member of the electrosurgery blade assembly such that the first end of the first conductive hollow tube is positioned near the first end of the non-conductive hollow tube member, a flexible non-conductive tube contained within at least a portion of the ultrapolar electrosurgery pencil which provides a gas to the first conductive hollow tube, and a plurality of electrical conductors (such as wires) for connecting the return electrode, the active electrode, and the first conductive hollow tube to an RF electrosurgical generator for activating the ultrapolar electrosurgery pencil.

In another exemplary embodiment of the ultrapolar telescopic electrosurgery pencil with argon beam capability of the present invention, the ultrapolar electrosurgery pencil with argon beam capability is telescopic and includes a handpiece member having first and second ends and a channel contained therein where the handpiece member functions as a hollow telescopic member, an electrosurgery blade assembly positioned within the first end of the handpiece member where the electrosurgery blade assembly includes a non-conductive planar member with opposing planar sides and a sharp cutting edge, a return electrode located on one opposing planar side, an active electrode located on the other opposing planar side, and a non-conductive hollow tube member positioned over a top of the non-conductive planar member and at least a portion of the return electrode, a first conductive hollow tube having a first end and a second end where at least a portion of the first conductive hollow tube is concentrically contained within the non-conductive hollow tube member of the electrosurgery blade assembly such that the first end of the first conductive hollow tube is positioned near the first end of the non-conductive hollow tube member, a flexible non-conductive tube contained within at least a portion of the ultrapolar electrosurgery pencil which provides a gas to the first conductive hollow tube, a plurality of electrical conductors (such as wires) for connecting the return electrode, the active electrode, and the first conductive hollow tube to an RF electrosurgical generator for activating the ultrapolar electrosurgery pencil, a second handpiece member with a second channel having first and second ends and opposing contact members positioned along an internal length of the second handpiece member such that the opposing contact members are located on an interior surface of the second handpiece member that defines the second channel wherein the second end of the handpiece member functioning as the hollow telescopic member is contained within the second handpiece member, a second conductive hollow tube contained within the second channel of the second handpiece member where the second conductive hollow tube is in telescopic communication with the first conductive hollow tube member contained within the handpiece member functioning as the hollow telescopic member, an active slidable contact member located on an exterior surface of the handpiece member functioning as the hollow telescopic member where the active slidable contact member is in communication with both the active electrode and one of the opposing contact members located on the interior surface of the second handpiece member, and a return slidable contact member located on an exterior surface of the handpiece member functioning as the hollow telescopic member where the return slidable contact member is in communication with both the return electrode and the other opposing contact member located on the interior surface of the second handpiece member.

The telescopic communication of the second conductive hollow tube and the first conductive hollow tube may result in the second conductive hollow tube having a diameter smaller than the first conductive hollow tube to enable the second conductive hollow tube to slide within the first conductive hollow tube. Alternatively, the telescopic communication of the second conductive hollow tube and the first conductive hollow tube may result in the first conductive hollow tube having a diameter smaller than the second conductive hollow tube to enable the first conductive hollow tube to slide within the second conductive hollow tube. The ultrapolar telescopic electrosurgery pencil with argon beam capability of the present invention may also include additional elements including, but not limited to, at least one support member for retaining the first conductive hollow tube within the channel of the handpiece member functioning as the hollow telescopic member where the same support member may further retain the active slidable contact member and the return slidable contact member on an exterior of the hollow telescopic member, and at least one support member for retaining the second conductive hollow tube within the second channel of the second handpiece member.

The terms electrode, contact, and contact member are used interchangeably throughout this specification to refer to conductive elements. It will be understood by those skilled in the art that the active and return electrodes/contacts/contact members as depicted in all of the drawing figures may be reversed—i.e. the electrodes/contacts/contact members shown as active electrodes/contacts/contact members could be return electrodes/contacts/contact members and the electrodes/contacts/contact members shown as return electrodes/contacts/contact members could be active electrodes/contacts/contact members. Reversing the types of electrodes/contacts/contact members would still result in the ultrapolar telescopic and non-telescopic electrosurgery pencils with argon beam capability having the same functional features and advantages.

The ultrapolar electrosurgery blade assembly in both the telescopic and non-telescopic ultrapolar electrosurgery pencils of the present invention may also include a return conductive insert and an active conductive insert both attached to an end of the non-conductive planar member located opposite the sharp cutting edge wherein the return conductive insert is in communication with the return electrode and the active conductive insert is in communication with the active electrode. In the ultrapolar telescopic electrosurgery pencil of the present invention, the return conductive insert is also in communication with the return slidable contact member and the active conductive insert is also in communication with the active slidable contact member.

In addition, the return electrode of the electrosurgery blade assembly in the ultrapolar telescopic and non-telescopic electrosurgery pencils with argon beam capability may comprise a conductive return layer and a conductive return projection extending from the conductive return layer where the conductive return projection is located within the non-conductive hollow tube member of the electrosurgery blade assembly and the first conductive hollow tube may include a conductive active projection extending from an end of the first conductive hollow tube member that is contained within the non-conductive hollow tube member of the electrosurgery blade assembly. This configuration would result in a gas, such as argon gas, that is passed through the first conductive hollow tube member and the non-conductive hollow tube member to be ionized by the conductive active projection of the first conductive hollow tube and the conductive return projection of the return electrode thereby resulting in providing an ionized gas for cutting or coagulating tissue.

The non-conductive hollow tube member and the non-conductive planar member of the electrosurgery blade assembly may each comprise a ceramic. The first conductive hollow tube and the second conductive hollow tube may be comprised of brass. Further, the non-conductive hollow tube member of the electrosurgery blade assembly may be positioned outside of the first end of the handpiece member in the non-telescopic pencil embodiment or the handpiece member that functions as the hollow telescopic member in the telescopic pencil embodiment. In addition, one or both of the first conductive hollow tube and the second conductive hollow tube may be insulated about their exterior outer surfaces. Further, the ultrapolar telescopic and non-telescopic electrosurgery pencils with argon beam capability of the present invention may also include a nozzle member which may be incorporated into the first end of the handpiece member in the non-telescopic pencil embodiment and the first end of the handpiece member that functions as the hollow telescopic member in the telescopic pencil embodiment. Still further, the nozzle member may be detachable and/or transparent.

Figure 3:
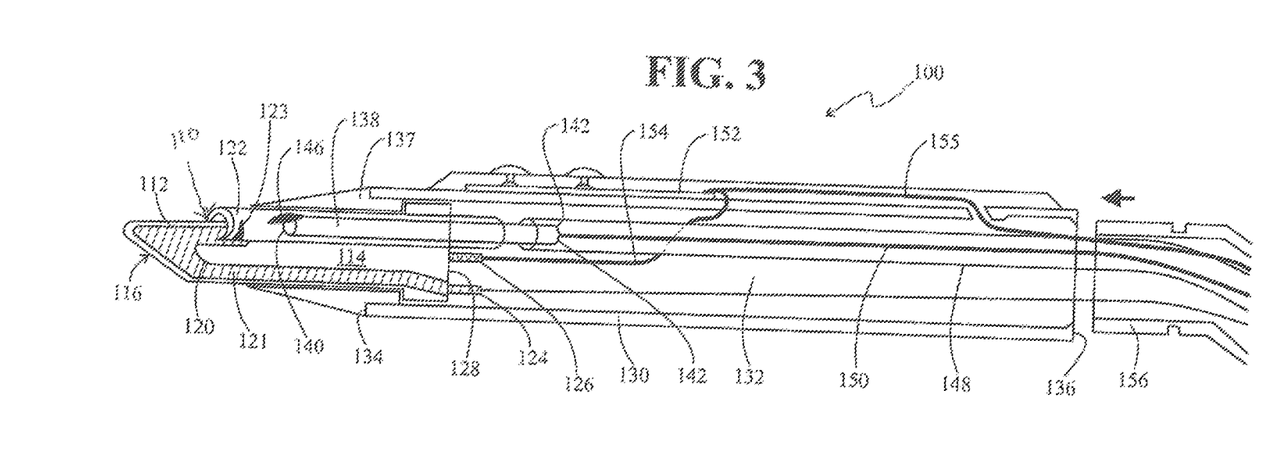
FIG. 3 is a perspective view of an exemplary embodiment of an ultrapolar electrosurgery pencil with argon beam capability of the present invention which shows the interior elements of the electrosurgery pencil and a swivel member which may be connected to the end of the ultrapolar electrosurgery pencil for facilitating use of the pencil while evacuating smoke and debris through the pencil and away from the surgical site by attaching a vacuum tube to the swivel member.
Figure 4:
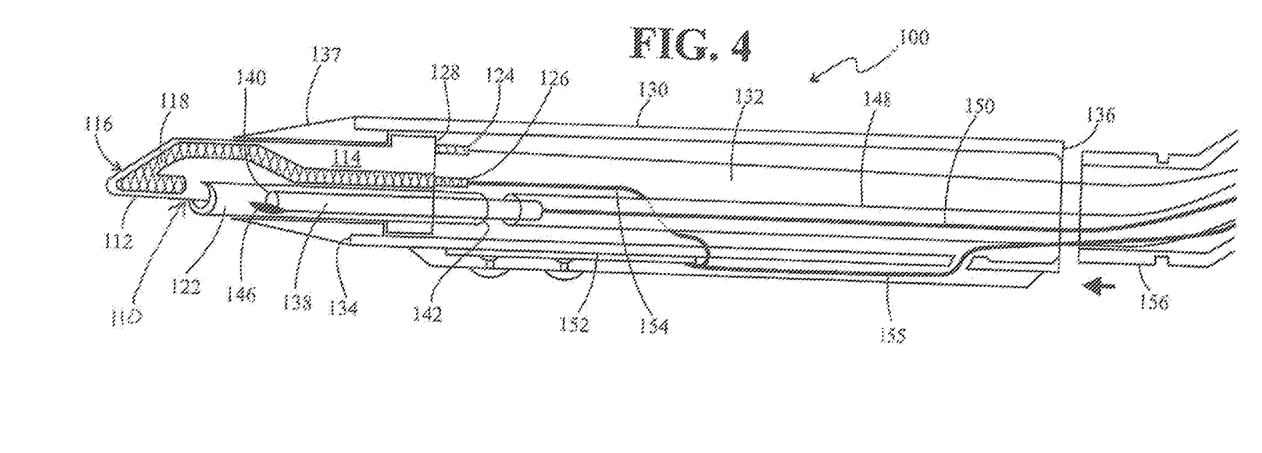
FIG. 4 is a perspective view of the exemplary embodiment of the ultrapolar electrosurgery pencil with argon beam capability depicted in FIG. 3 shown rotated 180 degrees to show the active and return electrodes of the electrosurgery blade assembly used in the ultrapolar electrosurgery pencil with argon beam capability located on opposite sides of the electrosurgery blade assembly.

It will also be understood by those skilled in the art that the return electrode in the telescopic pencil embodiment may be connected to a conductive tube within the handpiece member functioning as the hollow telescopic member that is telescopically engaged with a solid conductive rod within the second handpiece member as shown in FIGS. 3 and 4 of incorporated provisional patent application having Ser. No. 62/404,292 and utility patent application having Ser. No. 15/725,640. The present invention may also incorporate and/or substitute other embodiments of elements shown in FIGS. 3 and 4 of the patent applications having Ser. No. 62/404,292 and Ser. No. 15/725,640 that have similar functions to those elements which comprise the present invention. Embodiments of elements shown in FIG. 5 of Ser. No. 62/404,292 and Ser. No. 15/725,640 may also be incorporated and/or substituted for other embodiments of elements included in the present invention that have similar functions.

It will also be understood by those skilled in the art that functional elements (including the electrosurgery blade assembly) contained within, or contained partially within, the channel of the handpiece member functioning as the hollow telescopic member and/or the channel of the second handpiece member can be positioned in such a way as to enable smoke and debris created at the surgical site to be evacuated through the interior of the channel of the handpiece member functioning as the hollow telescopic member and the channel of the second handpiece member by connecting the second end of the handpiece member or second handpiece member, or connecting the swivel member; to an evacuation tube which is in turn connected to a vacuum source. Accordingly, the ultrapolar telescopic and non-telescopic electrosurgery pencils with argon beam capability also have the ability to evacuate smoke and debris from the surgical site.

DETAILED DESCRIPTION OF EXEMPLARY EMBODIMENTS

The exemplary embodiments of the ultrapolar telescopic and non-telescopic electrosurgery pencils with argon beam capability of the present invention for use in electrosurgical unit (ESU) monopolar and bipolar modes enable a user or surgeon to perform cutting with the sharp non-conductive tip of the electrosurgery blade of the pencil as well as coagulation of large areas of biological tissue by using the electrical contacts of the electrosurgery blade. The ultrapolar telescopic and non-telescopic electrosurgery pencils with argon beam capability of the present invention may also perform cutting with the active and return electrodes of the electrosurgery blade addition, a user or surgeon can use the ultrapolar telescopic and non-telescopic electrosurgery pencils with argon beam capability of the present invention to cut and coagulate tissue using ionized gas such as ionized argon gas. Further, a user or surgeon can use the ultrapolar telescopic and non-telescopic electrosurgery pencils of the present invention to simultaneously cut tissue with the sharp non-conductive cutting edge of the electrosurgery blade while coagulating tissue using ionized gas.

Exemplary embodiments of the ultrapolar telescopic and non-telescopic electrosurgery pencils having argon beam capability of the present invention include an ultrapolar electrosurgery blade assembly that has a non-conductive planar member having opposing planar sides and a sharp cutting edge, a return electrode located on one opposing planar side, an active electrode located on the opposite planar side, and a non-conductive hollow tube member positioned over a top of the non-conductive planar member and at least a portion of the return electrode. The return electrode may include a conductive return layer and a conductive return projection that is located within the non-conductive hollow tube member that enables a gas supplied from a conductive hollow tube to enter into the non-conductive hollow tube member to be ionized as it comes into contact with a conductive active projection extending from the conductive hollow tube and the conductive return projection of the return electrode. The cutting edge of the non-conductive planar member can form a sharp non-conductive cutting edge for cutting biological tissue while the active and return electrodes located on opposite planar side of the non-conductive planar member can be used to perform coagulation as well as cutting of biological tissue.

Figure 1:
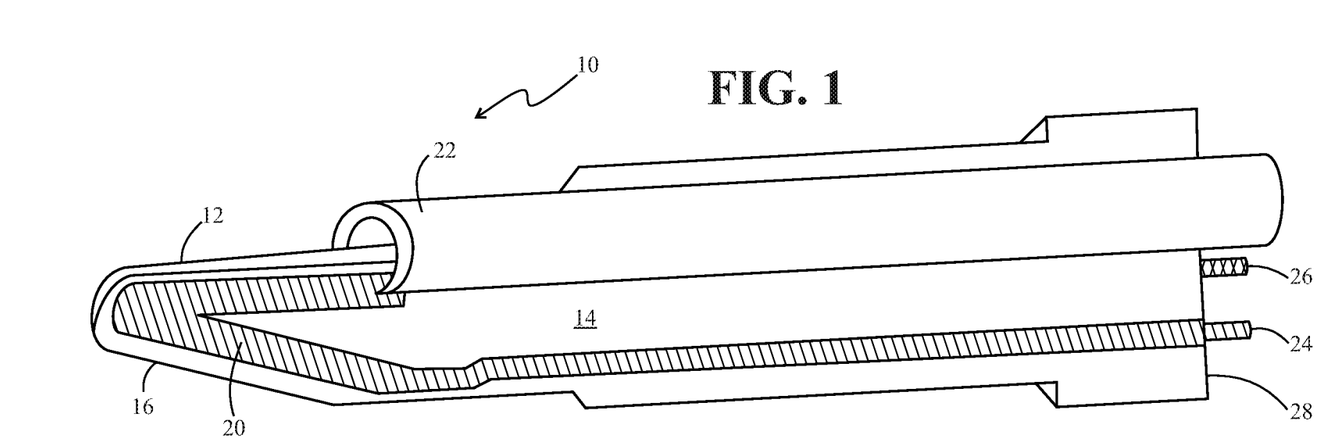
FIG. 1 is a perspective view of an exemplary embodiment of an ultrapolar electrosurgery blade assembly of the present invention.
Figure 2:
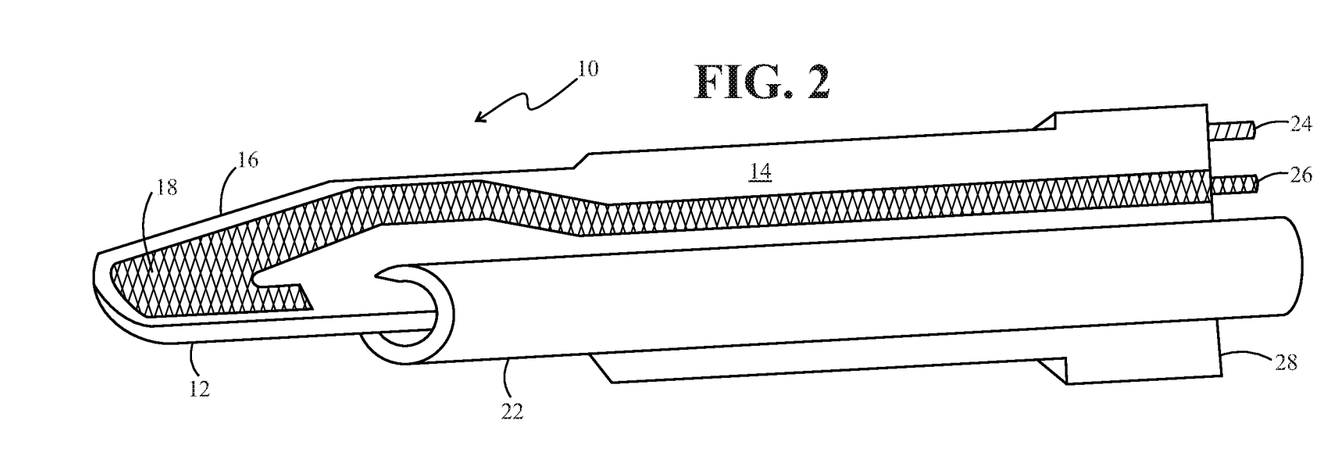
FIG. 2 is a perspective view of the exemplary embodiment of the ultrapolar electrosurgery blade assembly in FIG. 1 shown rotated 180 degrees to show the active and return electrodes located on opposite sides of the ultrapolar electrosurgery blade.

The identity of the elements/features that relate to the reference numbers shown in FIG. 1 and FIG. 2 are as follows:
   10 electrosurgery blade assembly
   12 non-conductive planar member
   14 opposing planar sides
   16 sharp cutting edge
   18 active electrode
   20 return electrode
   22 non-conductive hollow tube member
   24 return conductive insert
   26 active conductive insert
   28 end of non-conductive planar member opposite sharp cutting edge The identity of the elements/features that relate to the reference numbers shown in FIG. 3 and FIG. 4 are as follows:
   100 ultrapolar electrosurgery pencil with argon beam capability
   110 electrosurgery blade assembly
   112 non-conductive planar member
   114 opposing planar sides
   116 sharp cutting edge
   118 active electrode
   120 return electrode
   121 conductive layer (on return electrode)
   122 non-conductive hollow tube member
   123 conductive projection (on return electrode)
   124 return conductive insert (for connecting electrosurgery blade assembly to RF electrical generator [also known as an electrosurgical unit or ESU] for cutting with blade assembly and for ionization of gas)

126 active conductive insert (for connecting electrosurgery blade assembly to circuit board which is in turn connected to RF electrical generator for activating the ultrapolar electrosurgery pencil 100)

128 end of non-conductive planar member opposite sharp cutting edge 130 handpiece member 132 channel 134, 136 first and second ends (of handpiece member 130)

137 nozzle member (connected to first end of handpiece, member can be removable and/or transparent)

138 first conductive hollow tube 140, 142 first and second ends (of first conductive hollow tube 138)

146 conductive projection (extending from end of first conductive hollow tube 138 contained within non-conductive hollow tube member 122; gas (e.g. argon gas) is ionized between conductive projection 123 and conductive projection 146)

148 flexible, non-conductive tube (e.g. plastic) for supplying gas (e.g. argon gas) to first conductive hollow tube 138

150 active wire from RF electrosurgical generator extends through flexible non-conductive tube 148 and is connected to first conductive hollow tube 138 (for ionization of gas, such as argon gas)

152 circuit board (for activating ultrapolar electrosurgery pencil with argon beam capability 100)

154 active wire for connecting active electrode 118 of electrosurgery blade assembly 110 to circuit board 152

155 active wire for connecting circuit board 152 to RF electrosurgical generator 156 swivel member (connected to second end 136 of handpiece member 130)

Figure 5:
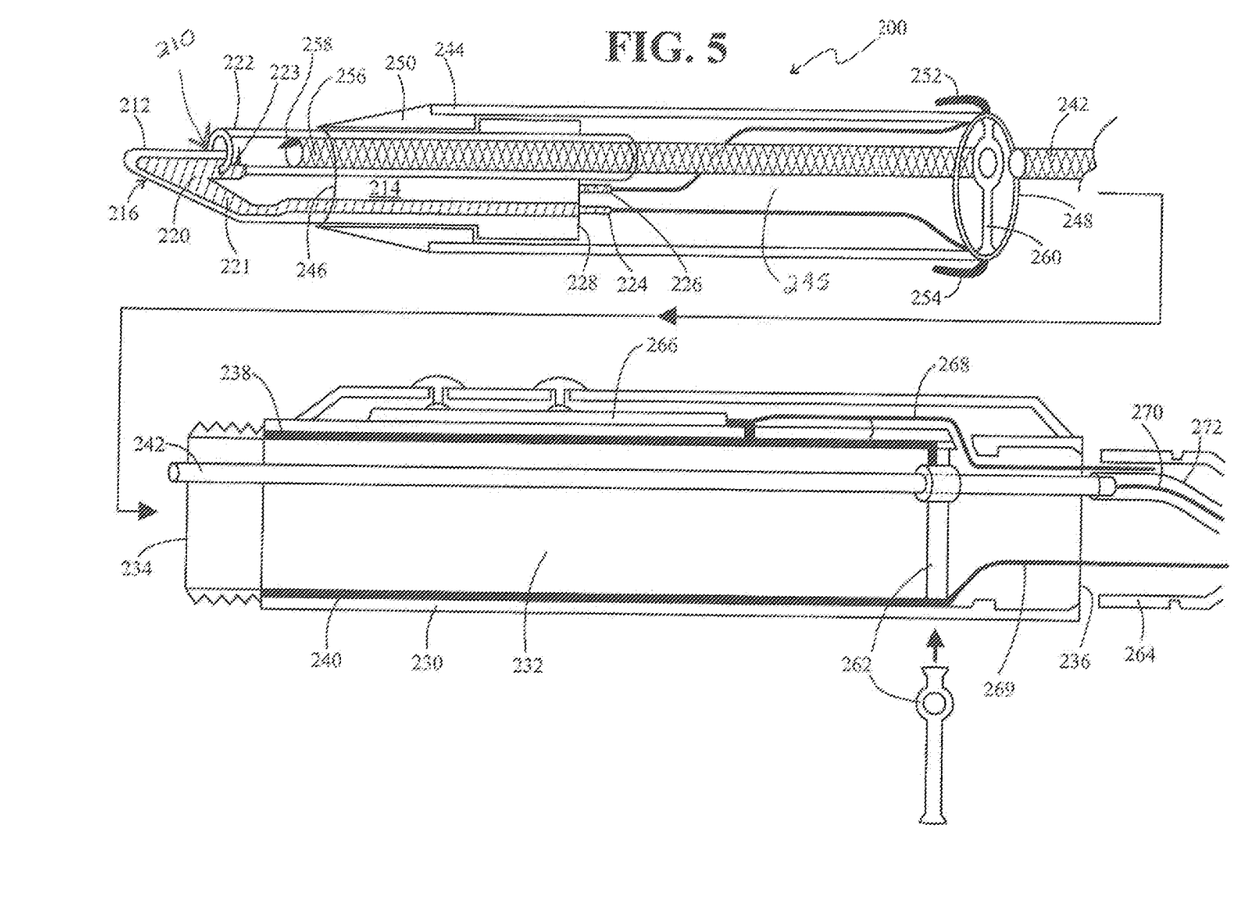
FIG. 5 is an exploded perspective view of an exemplary embodiment of an ultrapolar telescopic electrosurgery pencil with argon beam capability of the present invention which shows the interior elements of the electrosurgery pencil.
Figure 6:
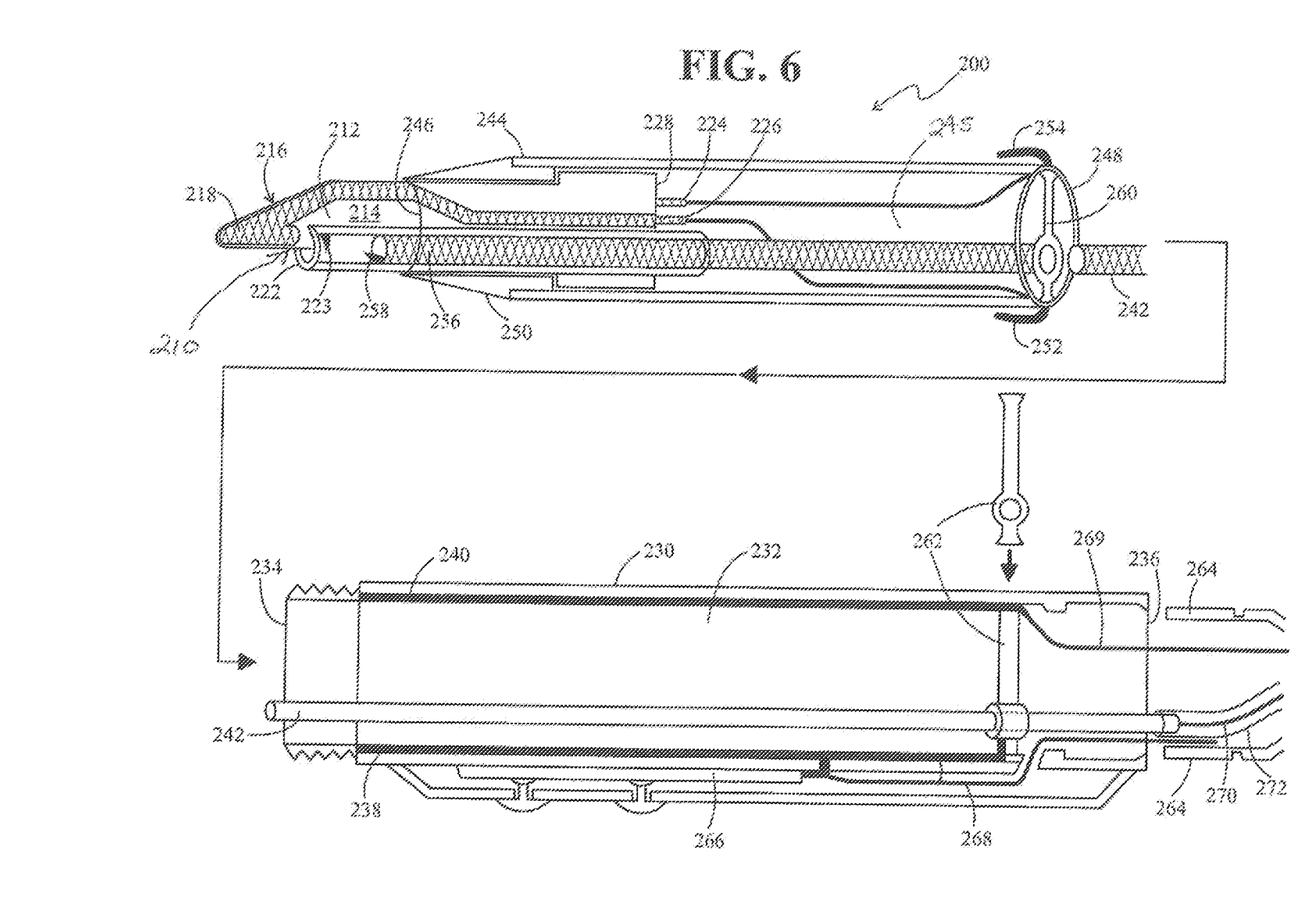
FIG. 6 is an exploded perspective view of the exemplary embodiment of the ultrapolar telescopic electrosurgery pencil with argon beam capability depicted in FIG. 5 shown rotated 180 degrees to show the active and return electrodes of the electrosurgery blade assembly used in the ultrapolar telescopic electrosurgery pencil with argon beam capability located on opposite sides of the electrosurgery blade assembly.

The identity of the elements/features that relate to the reference numbers shown in FIG. 5 and FIG. 6 are as follows:

200 ultrapolar telescopic electrosurgery pencil with argon beam capability 210 electrosurgery blade assembly 212 non-conductive planar member 214 opposing planar sides 216 sharp cutting edge 218 active electrode 220 return electrode 221 conductive layer (on return electrode)

272 non-conductive hollow tube member 223 conductive projection (on return electrode)

224 return conductive insert (for connecting electrosurgery blade assembly to RF electrical generator [also known as an electrosurgical unit or ESU] for cutting with blade assembly and for ionization of gas)

226 active conductive insert (for connecting electrosurgery blade assembly to circuit board which is in turn connected to RF electrical generator for activating ultrapolar telescopic electrosurgery pencil 200 and enabling; among other actions, cutting with blade assembly using low power)

228 end of non-conductive planar member opposite sharp cutting edge 230 second handpiece member 232 second channel 234; 236 first and second ends (of second handpiece member 230)

238, 240 opposing contact members (located along opposite interior lengths of second handpiece member 230)

242 second conductive hollow tube 244 handpiece member functioning as hollow telescopic member 245 channel 246, 248 first and second ends (of handpiece member functioning as hollow telescopic member 244)

250 nozzle member of handpiece member functioning as hollow telescopic member 244 (can be removable and/or transparent)

252 active slidable contact member (for active electrode on blade assembly; slides within and/or along opposing contact member 238)

254 return slidable contact member (for return electrode on blade assembly; slides within and/or along opposing contact member 240)

256 first conductive hollow tube (contained within handpiece member functioning as hollow telescopic member 244 and at least a portion contained within non-conductive hollow tube member of electrosurgery blade assembly 210)

258 conductive projection (extending from end of first conductive hollow tube 256 contained within non-conductive hollow tube member 222; gas (e.g. argon gas) is ionized between conductive projection 223 and conductive projection 258)

260 first support member for first conductive hollow tube 256 (may also support active slidable contact member 252 and return slidable contact member 254)

262 second support member for second conductive hollow tube 242 264 swivel member (connected to second end 236 of second handpiece member 230)

266 circuit board (for activating ultrapolar telescopic electrosurgery pencil with argon beam capability 200)

268 active wire from RE electrosurgical generator to circuit board (for activating ultrapolar telescopic electrosurgery pencil with argon beam capability 200)

269 wire connected to return electrode 220 which in turn is connected to RE electrosurgical generator 270 active wire from RE electrosurgical generator connected to second conductive hollow tube 242 which is in turn connected to first conductive hollow tube 256 (for ionization of gas, such as argon gas)

272 flexible, non-conductive tube for supplying gas (such as argon gas) from gas source to second conductive hollow tube 242 which is in turn connected to first conductive hollow tube 256

FIGS. 1 and 2 are opposing perspective views of an exemplary embodiment of an ultrapolar electrosurgery blade assembly 10 that comprises part of the ultrapolar telescopic and non-telescopic electrosurgery pencils of the present invention. Electrosurgery blade assembly 10 includes a non-conductive planar member 12 having opposing planar sides 14 and a sharp cutting edge 16, a return electrode 20 located on one opposing planar side 14, an active electrode 18 located on the opposite planar side 14, and a non-conductive hollow tube member 22 positioned over a top of the non-conductive planar member 12 and at least a portion of the return electrode 20. As shown in FIGS. 3 and 5, return electrode 20 includes a conductive layer 121, 221 and a conductive projection 123, 223 extending from the conductive layer 121, 221 such that the conductive projection 123, 223 is located within the non-conductive hollow tube member 122, 222. Ultrapolar electrosurgery blade assembly 10 also includes a return conductive insert 24 and an active conductive insert 26 that are both attached to an end 28 of the non-conductive planar member 12 located opposite the sharp cutting edge 16 such that the return conductive insert 24 is in communication with the return electrode 20 and the active conductive insert 26 is in communication with the active electrode 18.

FIG. 3 is a perspective view of an exemplary embodiment of an ultrapolar electrosurgery pencil with argon beam capability 100 of the present invention which shows the interior elements of the electrosurgery pencil and a swivel member 156 which may be connected to the end 136 of the ultrapolar electrosurgery pencil 100 for facilitating use of the pencil while evacuating smoke and debris through the pencil and away from the surgical site by attaching a vacuum tube to the swivel member 156. A perspective view of the exemplary embodiment of the ultrapolar electrosurgery pencil with argon beam capability 100 depicted in FIG. 3 shown rotated 180 degrees to show the active and return electrodes 118, 120 of the electrosurgery blade assembly used in the ultrapolar electrosurgery pencil with argon beam capability 100 located on opposite sides of the electrosurgery blade assembly is shown in FIG. 4, The ultrapolar electrosurgery pencil with argon beam capability 100 is non-telescopic and includes a handpiece member 130 having a first end 134, a second end 136, and a channel 132 contained therein, an electrosurgery blade assembly 110 positioned within the first end 134 of the handpiece member 130 where the electrosurgery blade assembly 110 includes a non-conductive planar member 112 with opposing planar sides 114 and a sharp cutting edge 116, a return electrode 120 located on one opposing planar side 114, an active electrode 118 located on the other opposing planar side 114, and a non-conductive hollow tube member 122 positioned over a top of the non-conductive planar member 112 and at least a portion of the return electrode 120, a first conductive hollow tube 138 having a first end 140 and a second end 142 where at least a portion of the first conductive hollow tube 138 is concentrically contained within the non-conductive hollow tube member 122 of the electrosurgery blade assembly 110 such that the first end 140 of the first conductive hollow tube 138 is positioned near the first end of the non-conductive hollow tube member 122, a flexible non-conductive tube 148 contained within at least a portion of the ultrapolar electrosurgery pencil 100 which provides a gas to the first conductive hollow tube 138, and a plurality of electrical conductors (such as wires 150, 154, 155) for connecting the return electrode 120, the active electrode 118, a circuit board 152, and the first conductive hollow tube 138 to an RF electrosurgical generator for activating the ultrapolar electrosurgery pencil 100.

The first conductive hollow tube 138 includes a conductive projection 146 and the return electrode 120 includes a conductive projection 123 where both the conductive projections 123, 146 are contained within the non-conductive hollow tube member 122 of the ultrapolar electrosurgery blade assembly 110. The return electrode may include a conductive layer 121 where the conductive projection 123 extends form the conductive layer 121 and the conductive projection 123 is located within the non-conductive hollow tube member 122. The ultrapolar electrosurgery blade assembly 110 includes a return conductive insert 124 and an active conductive insert 126 that are both attached to an end 128 of non-conductive planar member 112 located opposite sharp cutting edge 116 and return conductive insert 124 is in communication with return electrode 120 and active conductive insert 126 is in communication with active electrode 118, Handpiece member 130 may include a nozzle member 137 connected to the first end 134 of handpiece member 130 and nozzle member 137 may be removable and/or transparent. The non-conductive planar member 112 and the non-conductive hollow tube member 122 of ultrapolar electrosurgery blade assembly 110 may be made of a ceramic material while the first conductive hollow tube 138 may be made of brass.

FIG. 5 is an exploded perspective view of an exemplary embodiment of an ultrapolar telescopic electrosurgery pencil with argon beam capability 200 of the present invention which shows the interior elements of the electrosurgery pencil. FIG. 6 is an exploded perspective view of the exemplary embodiment of the ultrapolar telescopic electrosurgery pencil with argon beam capability 200 depicted in FIG. 5 shown rotated 180 degrees to show the active and return electrodes 218, 220 of the electrosurgery blade assembly 210 used in the ultrapolar telescopic electrosurgery pencil with argon beam capability 200 located on opposite sides of the electrosurgery blade assembly 210.

The ultrapolar telescopic electrosurgery pencil with argon beam capability 200 includes a handpiece member 244 having first and second ends 246, 248 and a channel 245 contained therein where the handpiece member 244 functions as a hollow telescopic member, an electrosurgery blade assembly 210 positioned within the first end 246 of the handpiece member 244 where the electrosurgery blade assembly 210 includes a non-conductive planar member 212 with opposing planar sides 214 and a sharp cutting edge 216, a return electrode 220 located on one opposing planar side 214, an active electrode 218 located on the other opposing planar side 214, and a non-conductive hollow tube member 222 positioned over a top of the non-conductive planar member 212 and at least a portion of the return electrode 220, a first conductive hollow tube 256 having a first end and a second end where at least a portion of the first conductive hollow tube 256 is concentrically contained within the non-conductive hollow tube member 222 of the electrosurgery blade assembly 210 such that the first end of the first conductive hollow tube 256 is positioned near the first end of the non-conductive hollow tube member 222, a flexible non-conductive tube 272 contained within at least a portion of the ultrapolar telescopic electrosurgery pencil 200 which provides a gas to the first conductive hollow tube 256, and a plurality of electrical conductors (such as wires 268, 269, 270) for connecting the return electrode 220, the active electrode 218, and the first conductive hollow tube 256 to an RF electrosurgical generator for activating the ultrapolar telescopic electrosurgery pencil 200. The ultrapolar telescopic electrosurgery pencil 200 further includes a second handpiece member 230 with a second channel 232 having first and second ends 234, 236 and opposing contact members 238, 240 positioned along an internal length of the second handpiece member 230 such that the opposing contact members 238, 240 are located on an interior surface of the second handpiece member 230 that defines the second channel 232. The second end 248 of the handpiece member 244 which functions as the hollow telescopic member is contained within the second handpiece member 230. A second conductive hollow tube 242 is contained within the second channel 232 of the second handpiece member 230 and the second conductive hollow tube 242 is in telescopic communication with the first conductive hollow tube 256 contained within the handpiece member 244 which functions as the hollow telescopic member. An active slidable contact member 252 is located on an exterior surface of the handpiece member 244 that functions as the hollow telescopic member and the active slidable contact member 252 is in communication with both the active electrode 218 and one of the opposing contact members 238 located on the interior surface of the second handpiece member 230. A return slidable contact member 254 is located on an exterior surface of the handpiece member 244 which functions as the hollow telescopic member and the return slidable contact member 254 is in communication with both the return electrode 220 and the other opposing contact member 240 located on the interior surface of the second handpiece member 230.

The telescopic communication of the second conductive hollow tube 242 and the first conductive hollow tube 256 may result in the second conductive hollow tube 242 having a diameter smaller than the first conductive hollow tube 256 to enable the second conductive hollow tube 242 to slide within the first conductive hollow tube 256. The ultrapolar electrosurgery blade assembly 210 includes a return conductive insert 224 and an active conductive insert 226 both attached to an end 228 of the non-conductive planar member 212 located opposite the sharp cutting edge 216. The return conductive insert 224 is in communication with the return electrode 220 and the return slidable contact member 254 and the active conductive insert 226 is in communication with the active electrode 218 and the active slidable contact member 252.

The ultrapolar telescopic electrosurgery pencil with argon beam capability 200 of the present invention also includes a first support member 260 for retaining the first conductive hollow tube 256 within the channel 245 of the handpiece member 244 which functions as the hollow telescopic member and the first support member 260 further retains the active slidable contact member 252 and the return slidable contact member 254 on an exterior of the hollow telescopic member 244. The ultrapolar telescopic electrosurgery pencil also includes a second support member 262 for retaining the second conductive hollow tube 242 within the second channel 232 of the second handpiece member 230. The flexible non-conductive tube 272 is connected to second conductive hollow tube 242 which is in turn connected to the first conductive hollow tube 256.

The first conductive hollow tube 256 includes a conductive projection 258 and the return electrode 220 includes a conductive projection 223 where both the conductive projections 223, 258 are contained within the non-conductive hollow tube member 222 of the ultrapolar electrosurgery blade assembly 210. The return electrode may include a conductive layer 221 where the conductive projection 223 extends form the conductive layer 221 and the conductive projection 223 is located within the non-conductive hollow tube member 222. Handpiece member 244 functioning as the hollow telescopic member may include a nozzle member 250 connected to the first end 246 of handpiece member 244 and nozzle member 250 may be removable and/or transparent. The non-conductive planar member 212 and the non-conductive hollow tube member 222 of ultrapolar electrosurgery blade assembly 210 may be made of a ceramic material while the first and second conductive hollow tubes 256, 242 may be made of brass.

The above description of exemplary embodiments of the invention shows various exemplary embodiments of the invention. These exemplary embodiments and modes are described and shown in sufficient detail to enable those skilled in the art to practice the invention and are not intended to limit the scope, applicability, or configuration of the invention in any way. Rather, the disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific enviroments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. An ultrapolar electrosurgery pencil with argon beam capability comprising:
   a handpiece member having a first end, a second end, and a channel contained therein;
   an electrosurgery blade assembly positioned within the first end of the handpiece member wherein the electrosurgery blade assembly includes a non-conductive planar member with opposing planar sides and a sharp cutting edge, a return electrode located on one opposing planar side, an active electrode located on the other opposing planar side, and a non-conductive hollow tube member positioned over a top of the non-conductive planar member and over at least a portion of the return electrode such that it does not cover or come into contact with the active electrode;
   a first conductive hollow tube having a first end and a second end wherein at least a portion of the first conductive hollow tube is concentrically contained within the non-conductive hollow tube member of the electrosurgery blade assembly such that the first end of the first conductive hollow tube is positioned near a first end of the non-conductive hollow tube member;
   a flexible non-conductive tube contained within at least a portion of the ultrapolar electrosurgery pencil which provides a gas to the first conductive hollow tube; and
   a plurality of electrical conductors for connecting the return electrode, the active electrode, and the first conductive hollow tube to an RE electrosurgical generator for activating the ultrapolar electrosurgery pencil.

2. The ultrapolar electrosurgery pencil of claim 1 wherein the first conductive hollow tube includes a conductive projection and the return electrode of the electrosurgery blade assembly includes a conductive projection wherein both conductive projections are contained within the non-conductive hollow tube member of the electrosurgery blade assembly.

3. The ultrapolar electrosurgery pencil of claim 1 wherein the handpiece member comprises a nozzle member connected to the first end of the handpiece member.

4. The ultrapolar electrosurgery pencil of claim 3 wherein the nozzle member is removable.

5. The ultrapolar electrosurgery pencil of claim 3 wherein the nozzle member is transparent.

6. The ultrapolar electrosurgery pencil of claim 1 wherein the non-conductive planar member and the non-conductive hollow tube member of the electrosurgery blade assembly comprise a ceramic material.

7. The ultrapolar electrosurgery pencil of claim 1 wherein the first conductive hollow tube comprises brass.

8. The ultrapolar electrosurgery pencil of claim 1 wherein the return electrode of the electrosurgery blade assembly comprises a conductive layer and a conductive projection extending from the conductive layer wherein the conductive projection is located within the non-conductive hollow tube member.

9. The ultrapolar electrosurgery pencil of claim 1 wherein the electrosurgery blade assembly further comprises a return conductive insert and an active conductive insert both attached to an end of the non-conductive planar member located opposite the sharp cutting edge wherein the return conductive insert is in communication with the return electrode and the active conductive insert is in communication with the active electrode.

10. An ultrapolar electrosurgery pencil with argon beam capability comprising:
a handpiece member having a first end, a second end, and a channel contained therein;
an electrosurgery blade assembly positioned within the first end of the handpiece member wherein the electrosurgery blade assembly includes a blade having a non-conductive sharp cutting edge, a return electrode, and an active electrode, and a non-conductive hollow tube member positioned over a top of the blade and over at least a portion of the return electrode such that it does not cover or come into contact with the active electrode;
a first conductive hollow tube having a first end and a second end wherein at least a portion of the first conductive hollow tube is concentrically contained within the non-conductive hollow tube member of the electrosurgery blade assembly such that the first end of the first conductive hollow tube is positioned near a first end of the non-conductive hollow tube member;
a flexible non-conductive tube contained within at least a portion of the ultrapolar electrosurgery pencil which provides a gas to the first conductive hollow tube; and
a plurality of electrical conductors for connecting the return electrode, the active electrode, and the first conductive hollow tube to an RF electrosurgical generator for activating the ultrapolar electrosurgery pencil.

11. The ultrapolar electrosurgery pencil of claim 10 wherein the first conductive hollow tube includes a conductive projection and the return electrode of the electrosurgery blade assembly includes a conductive projection wherein both conductive projections are contained within the non-conductive hollow tube member of the electrosurgery blade assembly.

12. The ultrapolar electrosurgery pencil of claim 10 wherein the handpiece member comprises a nozzle member connected to the first end of the handpiece member.

13. The ultrapolar electrosurgery pencil of claim 12 wherein the nozzle member is removable.

14. The ultrapolar electrosurgery pencil of claim 12 wherein the nozzle member is transparent.

15. The ultrapolar electrosurgery pencil of claim 10 wherein the non-conductive sharp cutting edge of the blade and the non-conductive hollow tube member of the electrosurgery blade assembly comprise a ceramic material.

16. The ultrapolar electrosurgery pencil of claim 10 wherein the first conductive hollow tube comprises brass.

17. The ultrapolar electrosurgery pencil of claim 10 wherein the return electrode of the electrosurgery blade assembly comprises a conductive layer and a conductive projection extending from the conductive layer wherein the conductive projection is located within the non-conductive hollow tube member.

18. The ultrapolar electrosurgery pencil of claim 10 wherein the electrosurgery blade assembly further comprises a return conductive insert and an active conductive insert both attached to an end of blade opposite the sharp non-conductive cutting edge of the blade wherein the return conductive insert is in communication with the return electrode and the active conductive insert is in communication with the active electrode.

\* \* \* \* \*